Figure 1:
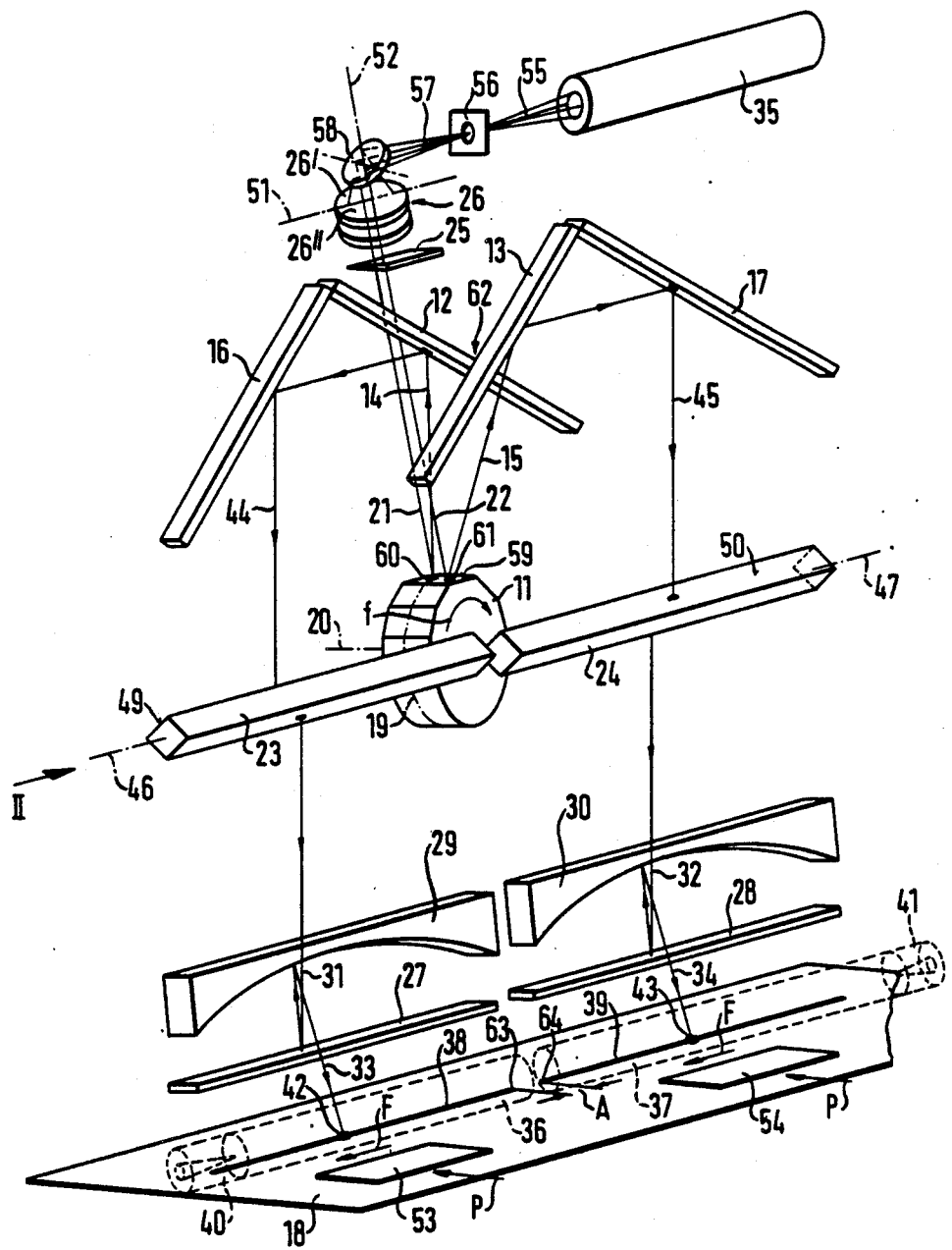

United States Patent [19]

Sick

[11] Patent Number: 4,681,453

[45] Date of Patent: Jul. 21, 1987

[54] OPTOELECTRONIC COMPARISON APPARATUS FOR STRUCTURES ON PLANE SURFACES OR FOR PLANAR STRUCTURES

[75] Inventor: Erwin Sick, Icking, Fed. Rep. of Germany

[73] Assignee: Erwin Sick GmbH Optik-Elektronik, Waldkirch, Fed. Rep. of Germany

[21] Appl. No.: 807,618

[22] Filed: Dec. 11, 1985

[30] Foreign Application Priority Data

Dec. 19, 1984 [DE] Fed. Rep. of Germany ....... 3446354

[51] Int. Cl.$^4$ .................. G01N 21/88; H05K 3/22; G01R 31/28
[52] U.S. Cl. .................................. 356/394; 350/6.8; 356/398
[58] Field of Search ............... 356/394, 398, 429, 430, 356/431; 350/6.8; 250/563, 571, 572

[56] References Cited

U.S. PATENT DOCUMENTS

| | | | |
|---|---|---|---|
| 3,944,369 | 3/1976 | Cuthbert et al. | 356/398 |
| 4,004,153 | 1/1977 | Obser et al. | 250/572 |
| 4,013,367 | 3/1977 | Nagao et al. | 250/572 |
| 4,065,212 | 12/1977 | Belleson et al. | 356/398 |
| 4,421,410 | 12/1983 | Karasaki | 356/394 |

FOREIGN PATENT DOCUMENTS 215399 11/1984 German Democratic Rep. ...................................... 250/563

*Primary Examiner*—R. A. Rosenberger
*Attorney, Agent, or Firm*—Townsend and Townsend

[57] ABSTRACT

An optoelectric comparison apparatus for structures on plane surfaces or for planar structures has a laser light source 35 the operational light beam of which is split into two component beams 21, 22 by an optical displacement device 26, 25 for laterally displacing part of a beam. These two component light beams 21, 22 impinge on the mirror surfaces of a mirror wheel 11 obliquely to the axis of rotation 20. Two mutually crossed flat first strip mirrors 12, 13 are arranged in the direction of the light reflected from the mirror wheel 11 and each receive only one of the emergent component light beams 14, 15. The emergent component light beams 14, 15 are deflected in substantially opposite directions where, in each case, a further plane second strip mirror 16, 17 is provided which reflects the light to the scanning surface parallel to the light beams 14, 15 which enter into the first strip mirrors 12, 13.

17 Claims, 3 Drawing Figures

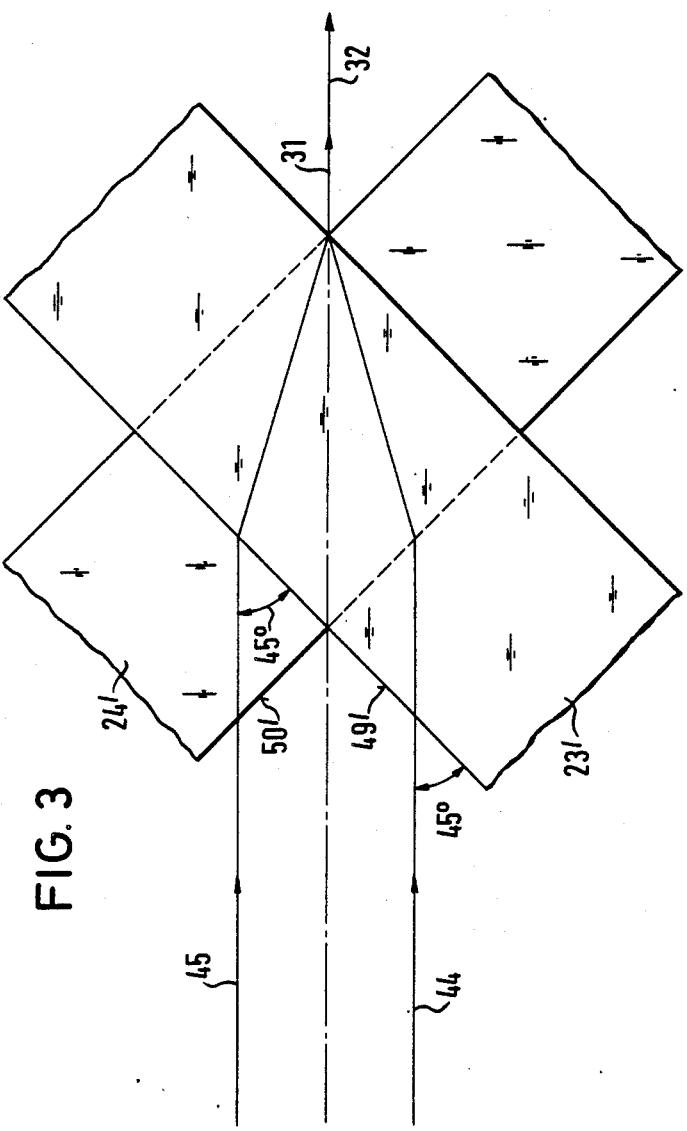

OPTOELECTRONIC COMPARISON APPARATUS FOR STRUCTURES ON PLANE SURFACES OR FOR PLANAR STRUCTURES

The invention relates to an optoelectronic comparison apparatus for structures on plane surfaces or for planar structures, the apparatus comprising a light source the operational light beam of which is split into two component beams by an optical displacement device for laterally displacing part of a beam, wherein said component beams impinge on a common cyclical light deflecting device, in particular a mirror wheel, preferably in a direction displaced from its axis of rotation, and are concentrated, after reflection at the light deflecting device, onto two points lying in a scanning surface containing the plates to be compared, wherein the two light points form, as a result of the cyclical movement of the light deflecting device, two spaced apart, non-overlapping scanning lines, and wherein a photoelectric light receiving device converts light originating from the scanning lines into electrical signals which are representative of the light intensity instantaneously leaving the points.

The plates which are to be compared with the aid of the apparatus of the invention are for example printed circuit boards or conductor boards which are to be investigated for discrepancies, i.e. faults, relative to a master circuit board.

An apparatus for comparing a test object with a master object by means of two movable scanning beams is already known (German patent DE-PS No. 14 23 597) wherein one scanning beam scans the master object and one the test object point, for point, line for line, and wherein the beams fall after passing through the objects, onto a photoelectric receiver arrangement which responds to the difference of the beam intensities.

In order to avoid, as far as possible, the effects of any dissimilar optical components in the two beam paths the light beam emerging from a light source is already subdivided in the known apparatus by a biprism into two laterally displaced component beams which are projected through a single image forming objective onto the reflecting surface of a mirror wheel, and the two light beads on the mirror wheel can either be displaced or superimposed by a further biprism. In the latter case the advantage is obtained that any irregularity of the reflecting surface of the mirror wheel has the same effects on the two reflected component beams. After the mirror wheel the component beams which initially overlap move apart from one another and finally provide separate scanning lines in two scanning planes parallel to one another.

The disadvantage of this known arrangement lies in the fact that the two scanning lines overlap one another over their entire lengths so that difficulties occur when scanning larger circuit boards because these circuit boards enter, when being displaced relative to the one scanning line, into the other scanning line, even after a relatively short feed path, where the master object or master board necessary for comparison purposes has to be arranged.

Admittedly the component beams present behind the light deflecting device can, in accordance with another embodiment of the known apparatus, be further decoupled by various deflecting mirrors, however this gives rise to the danger that distortion of the scanning light bead and/or of the scanning line can occur, in particular when generating relatively long scanning lines, and in particular to image distorsion (stereoscopic distortion) which considerably impairs the accuracy of the comparison.

The object of the present invention is thus to provide a comparatively simple optoelectronic comparison apparatus of the initially named kind which is relatively insensitive to shocks and vibration, by means of which two plates having a specific structure, in particular conductive circuit boards, and indeed a master board and a test board, can be optoelectronically compared with the highest accuracy while being spatially largely independent of one another.

In order to satisfy this object the invention provides that the incident component beams of light impinge obliquely to the axis of rotation onto the mirror surfaces of the light deflecting device; that two mutually crossed, plane, first strip mirrors are arranged directly alongside one another in the direction of the light reflected from the light deflecting device, with the incident component light beams just passing laterally past the first strip mirrors, each receive only one of the emergent light beams, and deflect the same into substantially opposite directions where, in each case, a further, plane, second strip mirror is provided which reflects the light to the scanning surface substantially parallel to the emergent light beams entering the first plane mirrors.

As a result of the construction of the invention the two scanning lines are generated on the scanning surface with a considerable spacing between their adjacent ends, but in exact alignment with one another, so that a test board and a master board can be fed parallel to one another to the adjacent scanning lines and perpendicular to the direction of the scanning lines, without the boards in any way hindering each other, because they have a clear lateral spacing perpendicular to their feed direction. The two boards are then scanned simultaneously and in parallel by the scanning beams so that an electrical signal is always present at the outputs of the two light receiving devices which makes it possible to electrically compare the same regions of the test article and the master article with one another.

It is particularly advantageous that all the optical components required to generate the two scanning beams up to and including the mirror wheel are identical. Only after the light deflecting device does each beam path come into contact with optical elements which are associated with it only, however, these optical elements are plane mirrors, plane parallel plates and strip-like concave mirrors which can be manufactured to the required degree of accuracy such that they do not introduce any marked irregularity into the two scanning lines.

The essential advantage of the invention is thus that a high degree of accuracy of the comparison is achieved despite the spatially significant decoupling of the two scanning positions.

A preferred practical embodiment is characterised in that the central plane of the light deflecting device which extends perpendicular to the axis of rotation of the light deflecting device passes symmetrically between the two first strip mirrors. In this arrangement each first and second strip mirror should in particular form an angle of 90° with one another. Furthermore, it is advantageous for the first strip mirrors to extend on both sides of the incident component beams by substantially equal amounts.

As a result of this construction it is ensured that the lateral decoupling of the two scanning beams does not lead to optical distortions, in particular to image distortion, and that minor vibrations of the apparatus cannot lead to errors during the comparison. The arrangement of the two strip mirror pairs for the lateral beam displacement is thus of particular importance.

The longitudinal axis of the first strip mirror advantageously subtends an angle of substantially 45° relative to the incident light beam when a light bead is at the center of the scanning line, whereby a particular compact arrangement is achieved, because in this arrangement the mirror wheel can, for example, be arranged beneath the two crossed first strip mirrors, i.e. overlap these mirrors.

An arrangement which is of particularly compact construction is furthermore achieved if the first strip-like mirrors (preferably) cross one another, essentially at approximately their half length. In this way the displacement of the two incident component light beams in the direction of the axis of rotation of the light deflecting device can be kept very small. It is in any case important that the one incident component light beam only impinges on one of the first strip-like mirrors, and that the other incident component light beam only impinges on the other of the two first strip-like mirrors, so that an exact and reproducable beam separation takes place here, and so that it is ensured that exactly the same light intensities permanently enter into the two beam paths.

A particular important further development of the invention consists in that at least one beam displacement device is provided between the second strip mirror and the scanning surface which cancels the beam displacement brought about by the device for laterally displacing the component beams. In particular provision can be made for each beam displacement device to consist of an inclined plane parallel strip plate.

In this manner the displacements of the two component beams produced by the device for displacing the component beams sideways is cancelled so that the two scanning lines lie on one and the same straight line.

A first preferred constructional embodiment is characterised in that the strip plates each consist of two transparent bars of square cross-section which are substantially aligned in the longitudinal direction, wherein the reflected component beams reflected from the second strip mirrors impinge substantially at 45° to the perpendicular onto the entry surfaces of the bars, and wherein the bars are so dimensioned with regard to their index of refraction and thickness, and are also displaced by a small amount both in the direction perpendicular to the reflected component beams and perpendicular to their longitudinal axes, that the emergent scanning beams extend in the same scanning plane.

A further possibility is that the strip plates consist of two transparent glass plates which are substantially aligned in the longitudinal direction and arranged at 90° to one another, wherein the reflected component beams impinge on their entry surfaces substantially at 45° to the perpendicular to the entry surface, and wherein the glass plates are so dimensioned with regard to their refractive index and thickness that the emergent scanning beams extend in the same scanning plane.

A displacement of the incident light beam can be particularly advantageously achieved if a lateral displacement device for the component beams is provided at the imaging objective arranged before the light deflecting device. In practice this can be achieved if the imaging objective is subdivided into two parts, in particular into two halves, with the line of separation being defined so that the one incident component beam emerges from the one half and the other incident component beam emerges from the other half of the imaging objective.

A particularly simple realisation of the lateral beam displacement consists in that an optical wedge is arranged directly in front of or behind the imaging objective in the area of at least one half, and deflects the incident beams away from the optical axis of the imaging objective.

Particularly precise scanning conditions at the scanning surface can be achieved if, in accordance with a further preferred embodiment, two strip-like plane mirrors are arranged near the scanning surface spaced apart behind one another in the longitudinal direction and optically perpendicular to the axis of rotation of the light deflecting device, wherein the two strip-like plane mirrors respectively receive one of the two scanning beams and reflect them to a strip-like hollow mirror arranged fractionally thereabove, and wherein each strip-like hollow mirror is respectively arranged spaced by its focal length from the reflecting surface of the light deflecting device, and forms a scanning beam which is displaced parallel to itself. The arrangement should in particular preferably be such that the strip-like plane mirrors and the strip-like hollow mirrors are aligned with one another in their longitudinal direction, and in that their neighbouring end faces are spaced from one another. Thus two completely identical and also identically arranged beam parallelization devices are present above both the test article and also the master article.

The light source is preferably a laser because in this way a particularly uniform intensity can be obtained over the entire beam cross-section, so that no irregularity is introduced into the two beam paths through the generation of the two component beams.

For receiving the light provision is advantageously made that two linear light receivers extending parallel to the scanning lines, in particular two light conducting rods, are provided as the light receiving device, and are each associated with one of the scanning lines, with a photoreceiver being provided at at least one end face of the light conducting rods.

Figure 2:
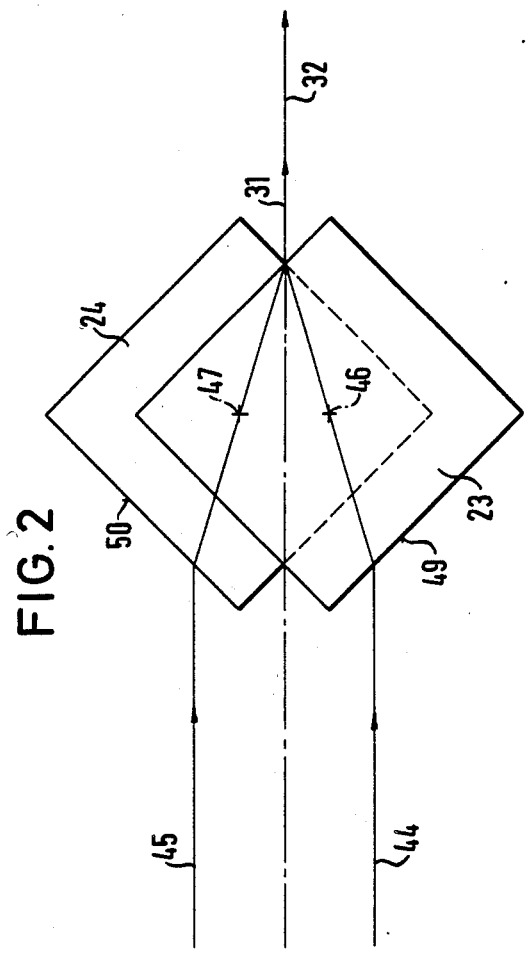

The invention will now be described in the following with reference to the drawings which show:

FIG. 1 a schematic perspective view of a preferred embodiment of an optoelectronic board surface comparison device, FIG. 2 an enlarged schematic end view in the direction of the arrow II in FIG. 1, and FIG. 3 an analogous end view of a further embodiment.

As seen in FIG. 1 a laser 35 generates, through the use of suitable beam widening means which are not shown, a light beam 55 with a substantially circular cross-section with a diameter of approximately 100 mm which has a uniform light intensity over the cross-section.

The beam 55 is given a precise circular cross-section by a beam forming stop or modal stop 56 with a circular opening provided in the light beam 55. The laser light beam 55 is convergent up to the modal stop 56. The so formed divergent light beam 57 with precise circular cross-section falls on a plane deflecting mirror 58 which deflects the light beam from the initial, substantially horizontal position vertically downwardly to an image forming objective 26 which gives the beams a slightly divergent course and concentrates the incident light beam 57 onto points 42, 43 on a preferably flat scanning surface 18. The image forming objective 26 is subdivided into two halves 26', 26" by an imaginary separating line 51 at which a strip-like aperture stop or diaphragm is preferably arranged, with an optical wedge 25 being arranged behind the half 26'. The wedge 25 provides the component light beam which passes through the half 26" with an angular displacement perpendicular to the optical axis 52 and to the dividing line 51 of the image forming objective 26, and this angular displacement is reproduced, somewhat exaggerated, in FIG. 1.

Two incident component light beams 21 and 22 separated by a small distance and with a small angular difference relative to one another are thus present after the wedge 25 which impinge on the straight reflecting surface 59 of the mirror wheel 11, the axis of rotation 20 of which extends perpendicular to the optical axis 52 and to the dividing line 51 of the image forming objective 26. Accordingly, two semicircular light beads 60, 61 which are spaced apart from one another by a small distance appear on the reflecting surface 59. The arrangement is expediently such that the one semicircular light bead 60 is arranged on the one side of the central plane 19 of the mirror wheel 11 and the other semicircular light bead 61 on the other side of the central plane. Accordingly, a spatial decoupling of the two incident component light beams 21, 22 has already taken place at the mirror wheel 11.

Above the mirror wheel 11, which can be set in rapid rotation in the direction of the arrow f there are two crossed first strip mirrors 12, 13, which are arranged directly alongside one another but slightly spaced apart at the crossing point 62. Their arrangement is such that the emergent component beam 14 reflected from the mirror wheel 11 impinges on the rear first strip mirror 12 and the other reflected emergent component beam 15 impinges on the front first strip mirror 13. The gap between the two emergent component beams 14, 15 overlaps somewhat with the two strip mirrors 12 and 13.

The upper ends of two second strip mirrors 16, 17 which form a roof-like arrangement with the associated first strip mirrors 12, 13 adjoin the upper ends of the first strip mirrors 12, 13, which subtend an angle of approximately 45° with the incident component beams 21, 22 at the instant when the light bead is at the center of the scanning path. The angle between the respective first and second strip mirrors 12, 16 and 13, 17 amounts to 90°. The projection of the second strip mirrors 17 onto the flat scanning surface 18 corresponds to the length of the scanning lines 38, 39. The length and design of the first and second strip mirrors 12, 13, 16, 17 are the same.

As a result of the combination of the first and second strip-like mirrors 12, 13, 16, 17 into an assembly resulting a ridge prism, the emergent component light beams 14, 15 are reflected from the first strip mirrors 12, 13 to the second strip mirrors 16, 17 from where they are deflected in the opposite direction to the scanning surface 18 in the form of displaced reflected component light beams 44, 45 which are laterally displaced but parallel to the incident component light beams.

As the beam is geometrically split either directly before or after the objective 26 the spacing of the centers of the beams is approximately the same as the half diameter of the pupil. The wedge 25 additionally brings about an angular difference whereby this spacing is enlarged and the separation is complete at the mirrors 12, 13. After reflection at the second mirrors 16, 17 this separation should not become larger but should instead be cancelled by beam displacements. In accordance with the invention the existing angular difference is first compensated by a slight tilting of the two ridge prism arrangements relative to one another, so that the two emergent beams 44, 45 extend in parallel planes. Only then is the existing beam displacement cancelled in the beam displacement bars 23, 24. For this purpose the reflected component beams 44, 45 enter into the entry surfaces 49, 50 of the two beam displacement bars 23, 24 of square section, in the manner shown in detail in FIG. 2. These bars are so arranged that the entry surfaces 49, 50 include an angle of approximately 45° with the reflected component beams 44, 45. However, whereas the reflected component beam 44 enters into the rear surface of the bar 23, the further reflected component beam 45 enters into the front surface 50 of the bar 24. The reflected component beam 44 is thus displaced forwardly while the reflected component beam 45 is displaced rearwardly. In this way, with a vertical displacement of the two beam axes 46, 47 in accordance with FIG. 2 (in FIG. 1 a horizontal displacement), scanning beams 31, 32 are formed which coincide in the side view of FIG. 2 after emergence from the bars 23, 24 and which define a scanning plane which extends perpendicular to the axis of rotation of the mirror wheel.

The scanning beams 31, 32 subsequently pass, close to the scanning surface 18, onto strip-like plane mirrors 27, 28 which extend parallel to the scanning surface 18 and to the bars 23, 24 and reflect the light obliquely to strip-like concave mirrors 29, 30 arranged directly above them and displaced somewhat to the rear. The concave mirrors 29, 30 are expediently of spherical construction, can however also have a cylindrical mirror characteristic.

The concave mirrors 29, 30 are optically disposed so that they are spaced by their focal lengths from the light beads 60, 61 on the mirror wheel 11, so that the scanning beams 33, 34 reflected from the concave mirrors 29, 30 are displaced parallel to themselves on rotation of the mirror wheel 11.

At the scanning surface 18 the scanning beams 33, 34 form scanning light beads at the points 42, 43 which, on rapid rotation of the mirror wheel, run in the direction of the arrow F over the surface of the scanning surface 18 and thus form the two scanning lines 38, 39 which lie exactly parallel to one another on one and the same straight line, and are aligned with one another and behind one another in the manner shown in FIG. 1.

A significant spacing A remains between the neighbouring end points 63, 64 of the two scanning lines 38, 39. A respective light receiving device which is only indicated in broken lines is provided parallel to each scanning line 38, 39 and consists in each case of a light conducting rod 36, 37 respectively at the ends of which a photomultiplier 40, 41 is mounted as a photoreceiver which transmits an electrical signal corresponding to the light which is incident on the side surface of the respective light conducting rod 36, 37.

A master circuit board 53 and a test circuit board 54 are arranged alongside one another on the scanning surface 18 and are so advanced in the direction of the arrow P perpendicular to the scanning lines 38, 39 that they are scanned linewise on moving beneath the scanning lines.

If care is taken that the same points of the two circuit boards 53, 54 are detected at the same instant by the scanning light beads at the points 42, 43, then it can be determined, by a comparison of the electrical output signals of the photoreceivers 40, 41, whether a particular irregularity which exceeds a certain dimension is present at a specific point of the two circuit boards 53, 54. Thus an exact point comparison of the surfaces of the two circuit boards can be relatively rapidly executed, because the scanning light frequency can be selected to be very high, and thus the two circuit boards 53, 54 can be transported relatively rapidly beneath the scanning device in the direction of the arrow P.

After the investigation of one circuit board 53 the master circuit board is pushed back into its initial position and the same comparison process then takes place with a further circuit board 54' which has just been produced.

As seen in FIG. 3 two plane parallel glass plates 23, 24' which are arranged at an angle of 90° can also be provided in place of the bars 24, 23 in FIGS. 1 and 2. The two reflected component light beams 44, 45 enter into the entry surfaces 49', 50' in analog manner at angles of 45°. The two exactly aligned scanning beams 31, 32 then emerge again at the crossing point of the two emergent surfaces of the glass plates 23', 24'.

I claim:

1. Optoelectronic comparison apparatus for structures on plane surfaces or for planar structures, the apparatus comprising a light source for generating an operational light beam which is split into first and second component beams by an optical displacement device for laterally displacing part of a beam, said component beams impinging on a cyclical light deflecting device displaced in a direction from its axis of rotation, and are directed, after reflection at the light deflecting device, onto first and second points lying on a scanning surface, which scanning surface includes the plane surfaces or planar structures to be compared, wherein the first and second light points form, as a result of the cyclical movement of the light deflecting device, first and second spaced apart, non-overlapping scanning lines, a photoelectric light receiving device for converting light originating from the scanning lines into electrical signals which are representative of the light intensity instantaneously leaving the points, the incident component beams of light impinging obliquely to the axis of rotation onto mirror surfaces of the light deflecting device, first and second mutually crossed, plane, first strip mirrors arranged directly alongside one another in the direction of the light reflected from the light deflecting device, the incident component light beams just passing laterally past the first strip mirrors, each receiving only one of the emergent light beams, and deflecting the same into substantially opposite directions where, in each case, further, plane, second strip mirrors are provided which reflect the light to the scanning surface substantially parallel to the emergent light beams entering the first strip mirrors.

2. Apparatus of claim 1, wherein a central plane of the light deflecting device which extends perpendicular to the axis of rotation of the light deflecting device passes symmetrically between the first and second first strip mirrors.

3. Apparatus of claim 1, wherein the first first strip mirror forms an angle of 90 degrees with the first second strip mirror and the second first strip mirror forms an angle of 90 degrees with the second second strip mirror.

4. Apparatus of claim 1, wherein the first strip mirrors extend on both sides of the incident component beams by substantially equal amounts.

5. Apparatus of claim 1, wherein the longitudinal axes of the first strip mirrors subtend an angle of substantially 45 degrees relative to the plane which is defined by the beam incident on the light deflecting device and its axis of rotation.

6. Apparatus of claim 1, wherein the first strip mirrors preferably cross one another essentially at approximately half way along them.

7. Apparatus of claim 1, wherein at least one beam displacement device is provided between the second strip mirrors and the scanning surface, which cancels the beam displacement brought about by the device for laterally displacing the component beams.

8. Apparatus of claim 7, wherein each beam displacement device comprises inclined plane parallel strip plates.

9. Apparatus of claim 8, wherein the strip plates each include first and second transparent bars of square cross-section which bars are substantially aligned in the longitudinal direction, wherein the reflected component beams reflected from the second strip mirrors impinge substantially at 45 degrees to the perpendicular onto the entry surfaces of the bars, and wherein the bars are so dimensioned with regard to their index of refraction and thickness and are also displaced by a small amount both in the direction perpendicular to the reflected component beams and perpendicular to their longitudinal axes that the emergent scanning beams extend in the same scanning plane.

10. Apparatus of claim 8, wherein the strip plates include first and second transparent glass plates which are substantially aligned in the longitudinal direction and arranged at 90 degrees to one another, wherein the reflected component beams impinge on their entry surfaces substantially at 45 degrees to the perpendicular to the entry surface, and wherein the glass plates are so dimensioned with regard to their refractive index and thickness that the emergent scanning beams extend in the same scanning plane.

11. Apparatus of claim 1, wherein the lateral displacement device for the component beams is provided at an imaging objective arranged before the light deflecting device.

12. Apparatus of claim 11, wherein the imaging objective is subdivided into a first part and a second part by a strip-like diaphragm arranged at an imaginary separating line extending optically perpendicular to the axis of rotation of the light deflecting device and perpendicular to the optical axis of the imaging objective, with the line of separation being defined so that the one incident component beam emerges from the one part and the other incident component beam emerges from the other part of the imaging objective.

13. Apparatus of claim 12, wherein an optical wedge is arranged directly in front of or behind the imaging objective in the area of the second part of the imaging objective, and deflects the incident beams away from the optical axis of the imaging objective.

14. Apparatus of claim 1, wherein first and second strip-like plane mirrors are arranged near the scanning surface spaced apart behind one another in the longitudinal direction and optically perpendicular to the axis of rotation of the light deflecting device, wherein the first and second strip-like plane mirrors each respectively receive one of the first and second scanning beams and reflect them onto strip-like concave mirrors arranged thereabove, and wherein each strip-like concave mirror is respectively arranged spaced by the focal length of that strip-like concave mirror from the reflecting surface of the light deflecting device and forms a scanning beam which is displaced parallel to itself.

15. Apparatus of claim 14, wherein the strip-like plane mirrors and the strip-like concave mirrors are aligned with one another in their longitudinal direction and their neighbouring end faces are spaced from one another.

16. Apparatus of claim 1, wherein the light source is a laser.

17. Apparatus of claim 1, wherein first and second linear light conducting rods extending parallel to the scanning lines, are each associated with one of the scanning lines, with a photoreceiver being provided at at least one end face of the light conducting rods.

* * * * *